US008294756B2

(12) United States Patent
Usami (10) Patent No.: US 8,294,756 B2
(45) Date of Patent: Oct. 23, 2012

(54) IMAGE PICKUP SYSTEM AND METHOD FOR MAINTAINING THE SAME

(75) Inventor: Hiroyuki Usami, Tokyo (JP)

(73) Assignee: Olympus Medical Systems Corp., Tokyo (JP)

( * ) Notice: Subject to any disclaimer, the term of this patent is extended or adjusted under 35 U.S.C. 154(b) by 727 days.

(21) Appl. No.: 12/404,491

(22) Filed: Mar. 16, 2009

(65) Prior Publication Data

US 2009/0244273 A1  Oct. 1, 2009

(30) Foreign Application Priority Data

Mar. 25, 2008  (JP) .................................. 2008-078829

(51) Int. Cl.
*A61B 1/04* (2006.01)
*A62B 1/04* (2006.01)

(52) U.S. Cl. ................. 348/76; 348/65; 348/71; 348/72; 348/73

(58) Field of Classification Search ............... 348/65–76
See application file for complete search history.

(56) References Cited

U.S. PATENT DOCUMENTS

| 6,710,442 | B1 * | 3/2004 | Lindgren et al. ............... 257/706 |
| 6,754,763 | B2 * | 6/2004 | Lin ................................. 710/317 |
| 6,785,873 | B1 * | 8/2004 | Tseng ............................. 716/102 |
| 7,132,664 | B1 * | 11/2006 | Crosetto ......................... 250/367 |
| 7,454,556 | B1 * | 11/2008 | Knapp ............................ 711/101 |
| 2004/0103341 | A1 * | 5/2004 | DeMeo et al. ..................... 714/6 |
| 2004/0133072 | A1 * | 7/2004 | Kennedy ......................... 600/109 |
| 2006/0261279 | A1 * | 11/2006 | Crosetto ......................... 250/367 |
| 2007/0070193 | A1 * | 3/2007 | Abe ................................. 348/65 |
| 2007/0282169 | A1 * | 12/2007 | Tsujita .......................... 600/160 |

FOREIGN PATENT DOCUMENTS

| CN | 101040767 A | 9/2007 |
| EP | 0 880 278 A1 | 11/1998 |
| EP | 1 719 445 A1 | 11/2006 |
| EP | 1 889 563 A1 | 2/2008 |
| JP | 2005065871 A * | 3/2005 |
| JP | 2006 033461 A | 2/2006 |
| JP | 2006-288753 | 10/2006 |
| JP | 2007 189429 A | 7/2007 |
| JP | 2007189429 A * | 7/2007 |
| WO | 2004/025963 A1 | 3/2004 |

OTHER PUBLICATIONS

Extended European Search Report dated May 11, 2011.

* cited by examiner

*Primary Examiner* — Hieu Hoang
(74) *Attorney, Agent, or Firm* — Scully, Scott, Murphy & Presser, P.C.

(57) ABSTRACT

An endoscope system, including: an endoscope for picking up an image of a subject and outputting an image pickup signal of the image; an external processor having a post-signal processing circuit which processes the image pickup signal inputted from the endoscope and generates a video signal that can be outputted to a monitor; and an output detecting circuit for detecting the presence or absence of an output of the image pickup signal and the presence or absence of an output of the video signal.

17 Claims, 11 Drawing Sheets

IMAGE PICKUP SYSTEM AND METHOD FOR MAINTAINING THE SAME

CROSS REFERENCE TO RELATED APPLICATION

This application claims the benefit of Japanese Patent Application No. 2008-078829 filed in Japan on Mar. 25, 2008, the contents of which are incorporated herein by this reference.

BACKGROUND OF THE INVENTION

1. Field of the Invention

The present invention relates to an image pickup system that includes an image pickup apparatus for picking up an image of a subject and outputting an image pickup signal of the image and a signal processing apparatus having a signal processing circuit for processing the image pickup signal inputted from the image pickup apparatus, and a method for maintaining the image pickup system.

2. Description of the Related Art

In the medical and other fields, so-called electronic endoscope apparatuses have been widely used, each of the apparatuses being provided with a charge coupled device (CCD) as a solid-state image sensing device at a distal end portion of an insertion section of the endoscope, and the CCD is used to pick up an image of a subject and the image from the endoscope is displayed on a monitor. Generally, the electronic endoscope apparatus is configured so that an analog image pickup signal from an electronic endoscope that has a CCD therein is transmitted to an external processor connected to the electronic endoscope so as to be exposed to various processes. That is, an image pickup apparatus for picking up an image of a subject and outputting an image pickup signal of the image outputs an analog image pickup signal, which is digitalized for processes in a signal processing apparatus.

To the contrary, a so-called electronic endoscope is known, in which for downsizing of a signal processing circuit, a part of the signal processing circuit is mounted to the endoscope, and an analog image pickup signal from a CCD is converted to a digital image pickup signal before the signal is outputted to an external processor which is a signal processing apparatus.

For example, Japanese Patent Application Laid-Open Publication No. 2006-288753 discloses an electronic endoscope system that has an endoscope with a CCD and an external processor removably connected to the endoscope, and the endoscope is provided with a digitalizing section that digitally processes a signal captured by the CCD, a data compressing section, a data transmitting section, and the processor is provided with a data receiving section, and a data decompressing section.

SUMMARY OF THE INVENTION

An image pickup system of the present invention includes: an image pickup apparatus for picking up an image of a subject and outputting an image pickup signal of the image; a signal processing apparatus having a signal processing circuit which processes the image pickup signal inputted from the image pickup apparatus and generates a video signal that can be outputted to a display section; and an output-detection section for detecting the presence or absence of an output of the image pickup signal and the presence or absence of an output of the video signal.

A method for maintaining an image pickup system of the present invention is a method for maintaining an image pickup system having an image pickup apparatus for picking up an image of a subject and outputting an image pickup signal of the image, and a signal processing apparatus having a signal processing circuit which processes the image pickup signal via an electrically connectable connector section from the image pickup apparatus and generates a video signal that can be outputted to a display section, including: a video signal detection step for detecting the presence or absence of an output of the video signal; a connection detection step for detecting the presence or absence of an electrical connection at the connector section; and an image pickup signal detection step for detecting the presence or absence of an output of the image pickup signal.

DETAILED DESCRIPTION OF THE PREFERRED EMBODIMENTS

First Embodiment

Figure 1:
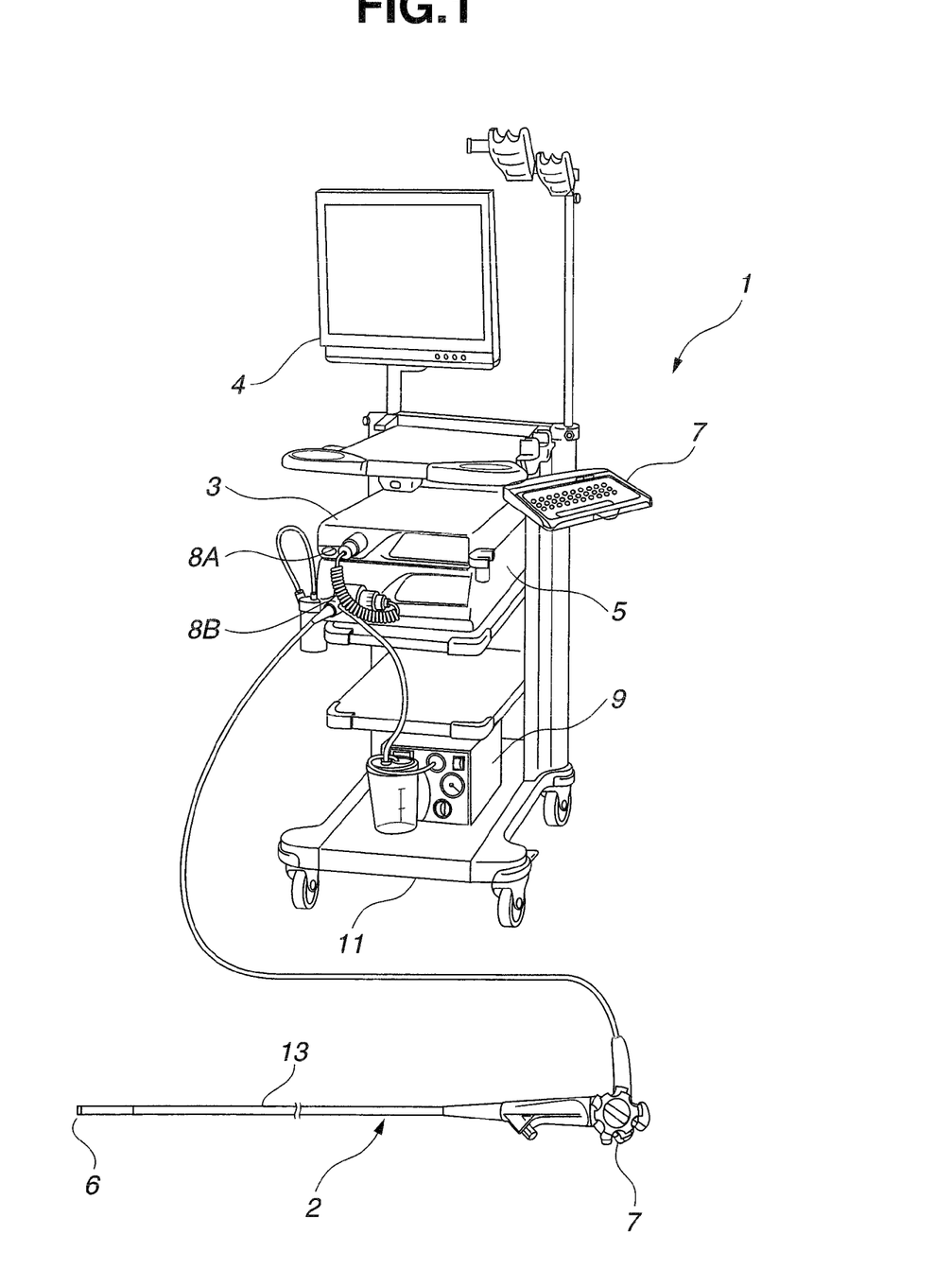
FIG. 1 is an external view showing a configuration of an endoscope system of a first embodiment.
Figure 2:
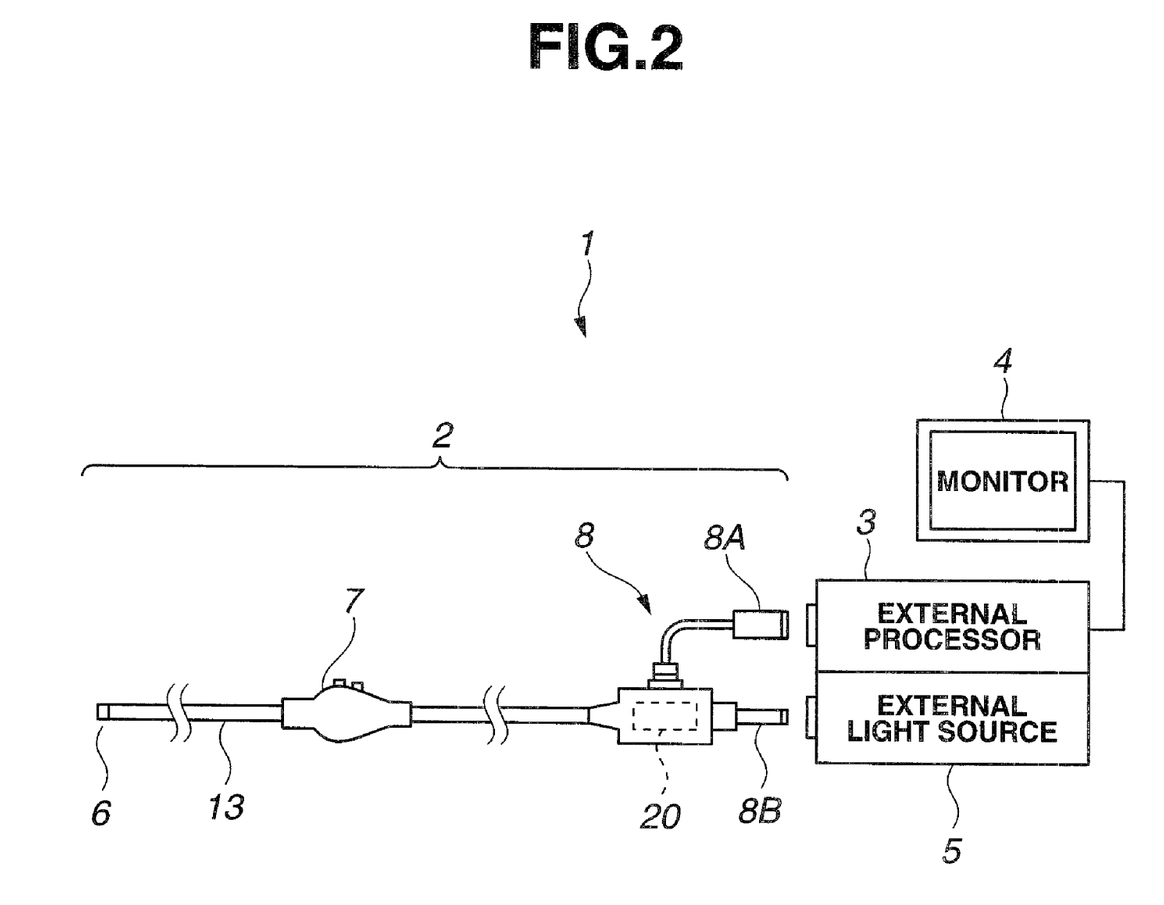
FIG. 2 is an illustrative diagram illustrating a configuration of the endoscope system of the first embodiment.
Figure 3:
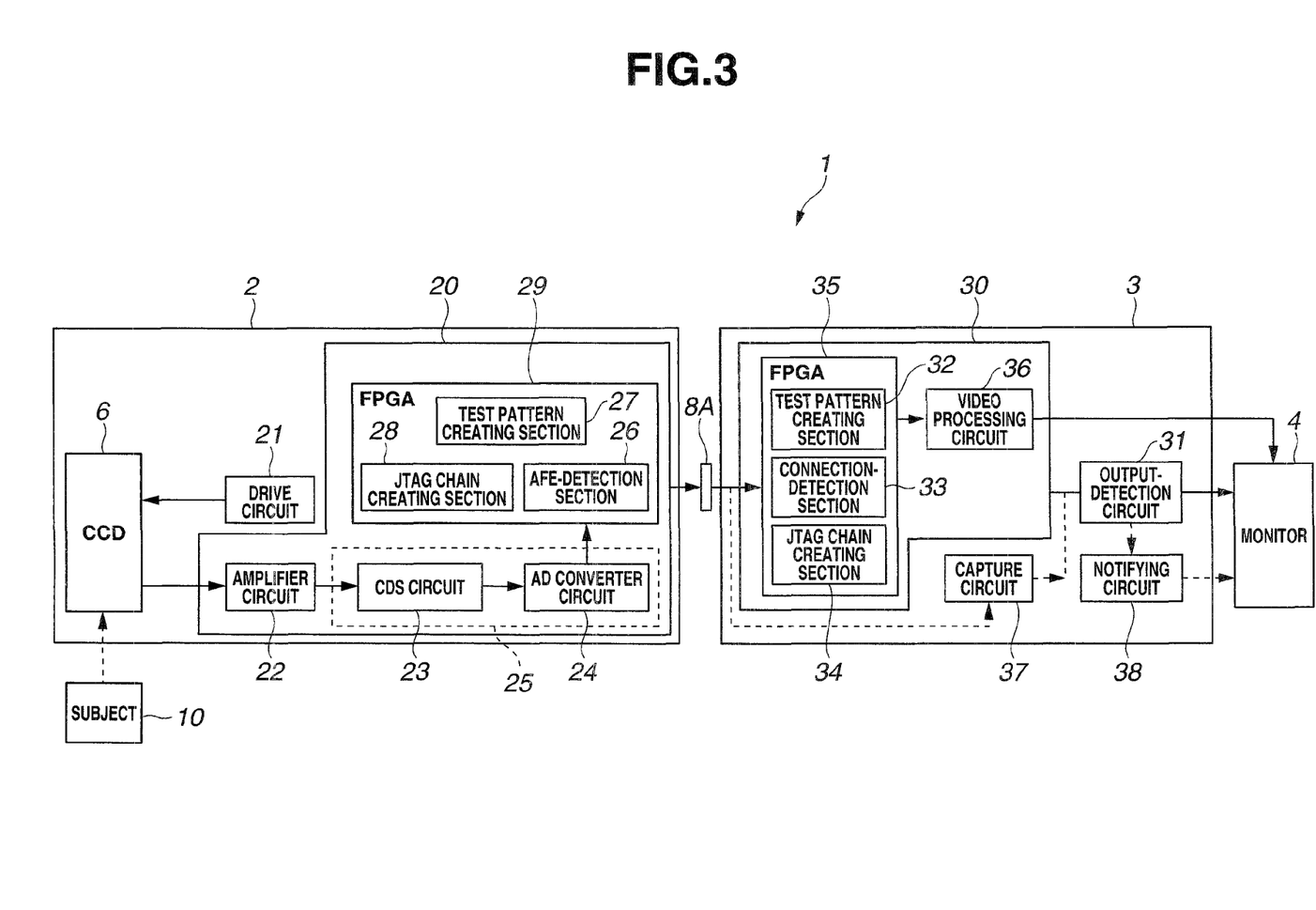
FIG. 3 is a block diagram illustrating a configuration of the endoscope system of the first embodiment.

Now, with reference to FIGS. 1 to 3, an endoscope system 1 of a first embodiment according to the present invention will be explained below. FIG. 1 is an external view showing a configuration of the endoscope system 1 of the present embodiment; FIG. 2 is an illustrative diagram illustrating a configuration of the endoscope system 1; and FIG. 3 is a block diagram illustrating a configuration of the endoscope system 1.

As shown in FIG. 1, the endoscope system 1 of the present embodiment includes: an endoscope 2 (hereinafter, also referred to as "scope") having an elongated insertion section 13 which is inserted into a body cavity for picking up an image of a region to be observed with a CCD 6 provided at the distal end portion thereof, and an operation section 7 with which an operator operates the endoscope; a light source apparatus 5 for supplying an illumination light to the endoscope 2; an external processor 3 for processing an image pickup signal from the endoscope 2 and causing a monitor 4 which is a display section to display the image or the like from the endoscope; an air/water pump 9 for supplying air and water; and the operation section 7 with which an operator inputs information, and these apparatuses are mounted to a rack 11. The endoscope 2 is removably connected to the external processor 3 via a connector section 8A, and to the light source apparatus 5 via a connector section 8B, and also connected to the air/water pump 9 via the connector section 8B.

As shown in FIG. 2, when the CCD 6 arranged at the distal end portion of the insertion section 13 outputs an analog image pickup signal, the analog image pickup signal is inputted to a pre-processing circuit 20 arranged at the connector section 8 of the endoscope 2 via a transmission cable (not shown) inserted through the insertion section 13, and is processed in the pre-processing circuit 20 to be outputted as a digital image pickup signal to the external processor 3. In FIG. 2, the pre-processing circuit 20 is arranged at the connector section 8, but may be arranged at the operation section 7, or may be divided and arranged at both of the operation section 7 and the connector section 8 for example, as long as the pre-processing circuit 20 is arranged at the endoscope 2.

Next, with reference to FIG. 3, a configuration of the endoscope system 1 of the present embodiment will be explained below in more detail. In the endoscope system 1, the CCD 6 driven by a drive circuit 21 picks up an image of a subject 10 in a body cavity, and outputs an analog image pickup signal of the image to the pre-processing circuit 20. The pre-processing circuit 20 includes an amplifier circuit 22, a CDS circuit 23, an AD converter circuit 24, and a first FPGA 29. The FPGA is the abbreviation for Field Programmable Gate Array, and is a programmable integrated circuit that can be used as a circuit for a desired operation by programming a desired software.

The analog image pickup signal passes through the CDS (correlated double sampling) circuit 23 via the amplifier circuit 22 to remove CCD noise included in the signal, and is converted to a digital image pickup signal such as a 12-bit digital image pickup signal in the AD converter circuit 24. The digital image pickup signal is transmitted to a second FPGA 35 on the external processor 3 side via the first FPGA 29 and the connector section 8A to be inputted to a post-processing circuit 30. The digital image pickup signal is processed in the post-processing circuit 30 to be outputted to the monitor 4 as a video signal, so that the image of the subject 10 by the endoscope is displayed on the monitor 4.

As shown in FIG. 3, the endoscope system 1 includes a detection circuit for, in case of a failure, detecting a part of the failure. The first FPGA 29 of the endoscope 2 is configured with a test pattern generating section 27 that is provided with a test pattern signal outputting function for generating a test pattern signal of a digital image pickup signal using a program, a JTAG chain creating section 28, and an AFE-detection section 26. The JTAG chain means a circuit that connects input and output ports in series to perform a boundary scan test based on JTAG standard. The AFE (Analog Front End) 25 is an element having a circuit for converting analog image data to digital data with peripheral circuits incorporated therein, and outputs a predetermined number of bit of, for example 12-bit, digital pickup image signals. The AFE-detection section 26 detects a normal operation of the AFE 25 when there is not a bit drop in the digital image pickup signals outputted from the AFE 25, that is, when the number of bits of the digital image pickup signal is equal to a predetermined number of bits.

The second FPGA 35 of the external processor 3 is configured with a test pattern generating section 32 that is provided with a test pattern signal outputting function for generating a test pattern signal of a digital image pickup signal, a JTAG chain creating section 34, and a connection-detection section 33. The connection-detection section 33 forms a consecutive wire circuit with the JTAG chain creating section 28 of the first FPGA 29 and the JTAG chain creating section 34 of the second FPGA 35 via the connector section 8A so as to detect any electrical connection failure at the connector section 8A. The external processor 3 further includes a capture circuit 37, instead of the post-processing circuit 30, for capturing an image data from the digital image pickup signal. The digital image pickup signal is processed in one of the post-processing circuit 30 and the capture circuit 37 using a switch (not shown) for processing.

The endoscope system 1 has an output-detection circuit 31 which is an output-detection section for detecting the presence or absence of an output signal to the monitor 4. The output-detection circuit 31 may be, as shown in FIG. 3, incorporated in the external processor 3, or may be a separated member. The output-detection circuit 31 is able to detect the presence or absence of an output of the image pickup signal from the endoscope 2, that is, a digital image pickup signal, and the presence or absence of an output of the video signal output from the post-processing circuit 30, by detecting the presence or absence of an output signal to the monitor 4, as will be explained later.

Furthermore, the endoscope system 1 preferably includes a notifying circuit 38 which is a section for notifying at least one of the detection results from the output-detection circuit 31, the connection-detection section 33, and the AFE-detection section 26. The notifying circuit may be, as shown in FIG. 3, incorporated in the external processor 3, or may be a separated member. The notifying circuit 38 may use the monitor 4 for notifying, and may include a notifying section that uses voice and the like (not shown).

As described above, the endoscope system 1 is an image pickup system including: the endoscope 2 which is an image pickup apparatus for picking up an image of the subject 10 and outputting an image pickup signal of the image; the external processor 3 which is a signal processing apparatus having the post-processing circuit 30 as a signal processing circuit for processing the image pickup signal inputted from the endoscope 2 and generating a video signal that can be outputted to the monitor 4; and the output-detection circuit 31 which is an output-detection section for detecting the presence or absence of an output of the image pickup signal and the presence or absence of an output of the video signal.

Figure 4A:
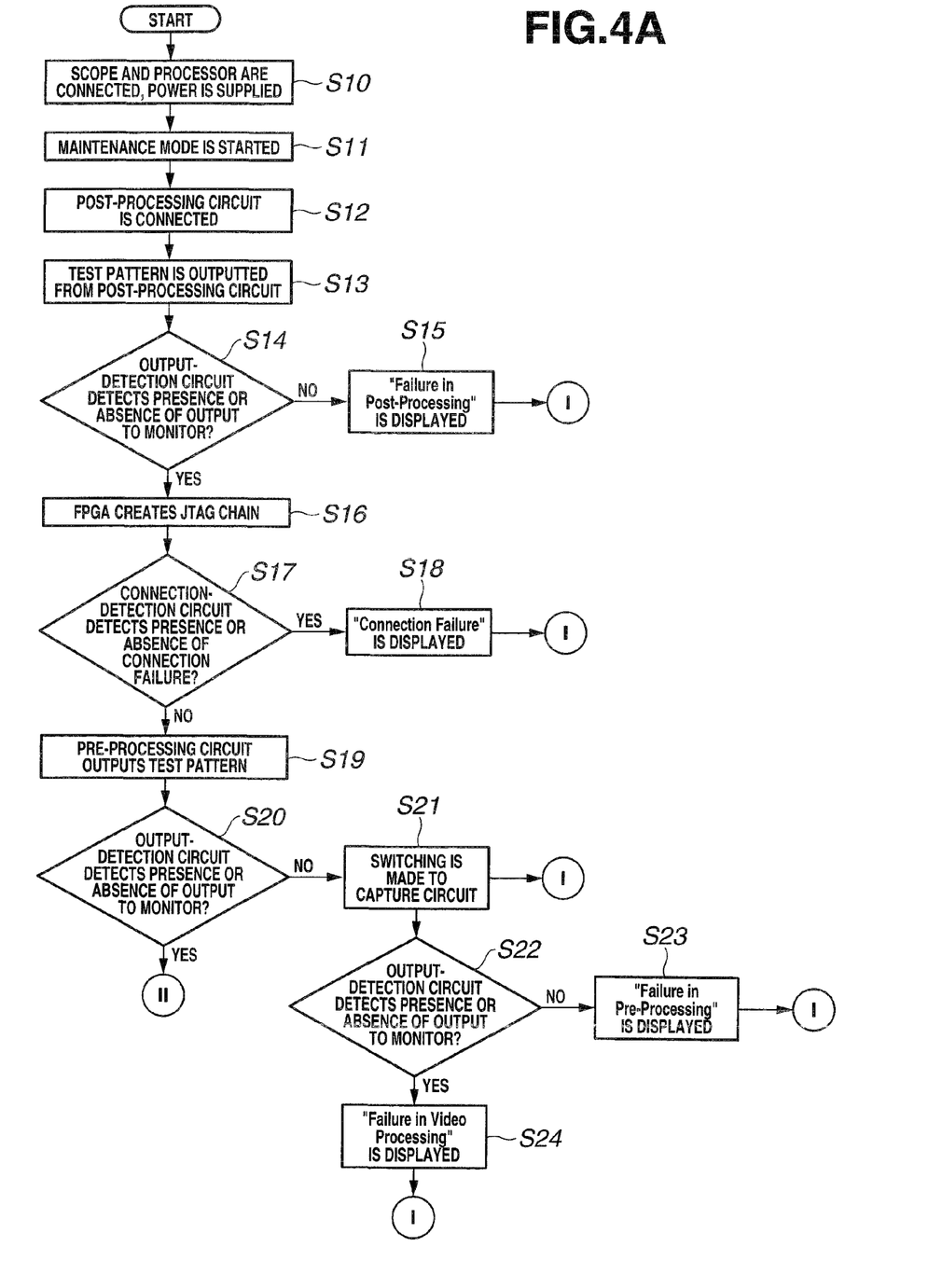
FIG. 4A is a flowchart illustrating a check flow of the endoscope system of the first embodiment.
Figure 4B:
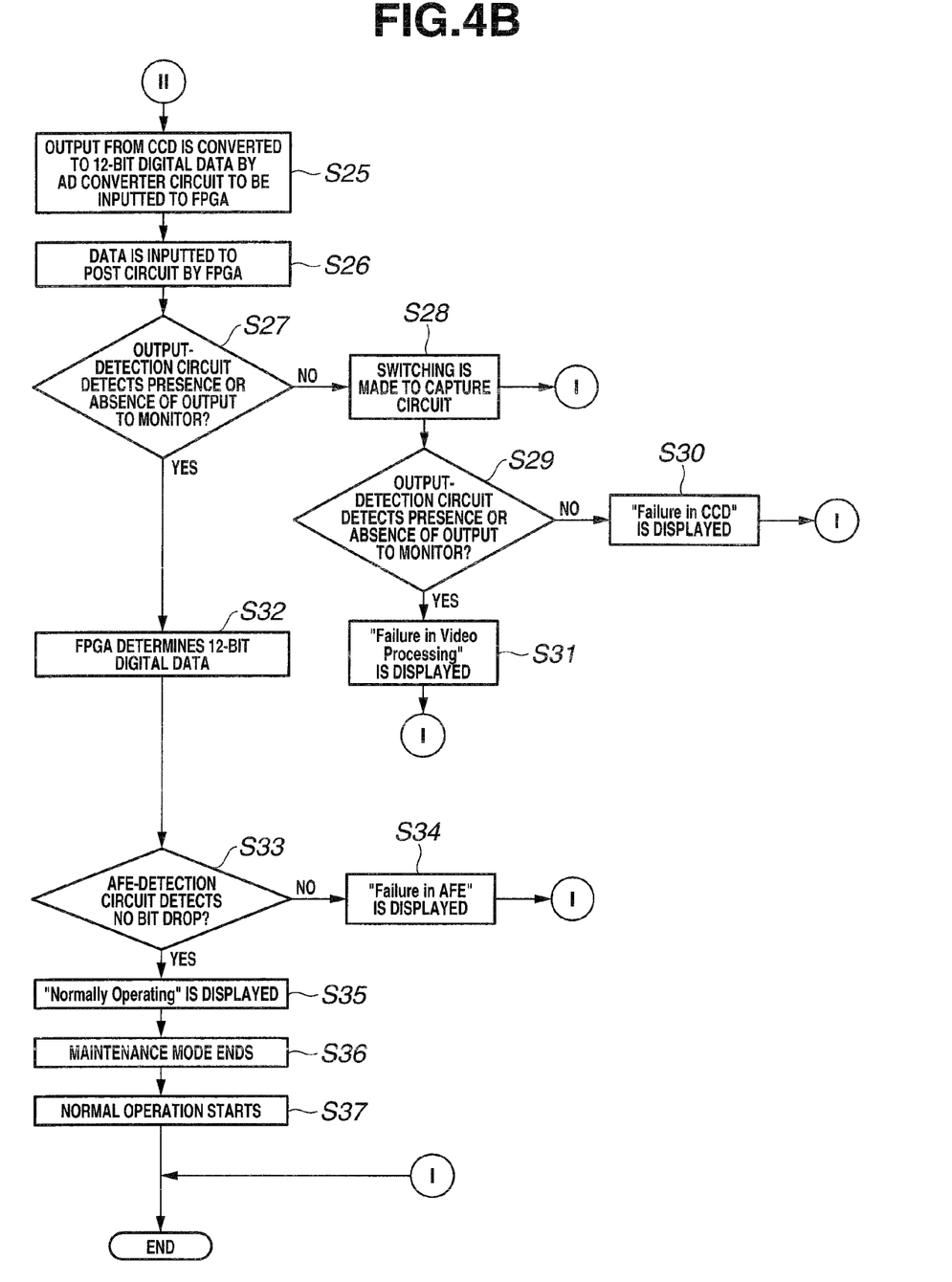
FIG. 4B is a flowchart illustrating a check flow of the endoscope system of the first embodiment.

Next, with reference to FIG. 4A and FIG. 4B, the flow of a maintenance process of the endoscope system 1 will be explained below. FIG. 4A and FIG. 4B are flowcharts illustrating the flow of a maintenance process of the endoscope system 1.

As shown in FIG. 4A and FIG. 4B, the endoscope system 1 checks in order every part of the system for failure. When a failure is found, the part of the failure is notified.

<Step S10>

The endoscope 2 is connected to the external processor 3. Then, the endoscope system 1 is powered. That is, the endoscope 2, the external processor 3, and the monitor 4 are supplied with power.

<Step S11>

The endoscope system 1 starts a maintenance mode that is an operation mode for performing a series of self-check processes to find any failed part in the endoscope system 1.

<Step S12>

The endoscope system 1 makes a switching to the post-processing circuit 30 between the post-processing circuit 30 and the capture circuit 37. As described above, the switching operation is performed using a switch (not shown) or the like.

<Step S13>

The test pattern generating section 32 of the post-processing circuit 30 outputs a test pattern signal.
<Step S14>
The output-detection circuit 31 detects the presence or absence of an output of the test pattern signal from the post-processing circuit 30. That is, the step S14 is a video signal detection step for detecting the presence or absence of an output of the video signal from the post-processing circuit 30, and also is a test pattern signal detection step for detecting the presence or absence of a test pattern signal.

Without any outputted test pattern signal (No), at step S15, the notifying circuit 38 displays a display of "Failure in Post-Processing" on the monitor 4 as a notification.

With an outputted test pattern signal (Yes), at step S16, a check is performed on the next part.
<Step S16>
The JTAG chain creating sections 28 and 34 individually create a JTAG chain that connects the input-output lines between the FPGA 29 and the FPGA 35 in series. That is, the ends of a plurality of signal wires in connection via the connector section 8A are connected to each other so that the ends are so-called daisy-chained as one wire functionally. Among the input-output lines of the JTAG chain creating section 34, two lines form the ends of JTAG chain that are connected to the connection-detection section 33.
<Step S17>
The connection-detection section 33 is able to detect a connection failure somewhere between the FPGA 29 and the FPGA 35 when the JTAG chain is OPEN, that is, when there is a continuity failure in the JTAG chain. In other words, the step S17 is a connection-detection step for detecting the presence or absence of an electrical connection at the connector section 8A. When the connection-detection section 33 detects a connection failure (Yes), at step S18, the notifying circuit 38 displays a display of "Connection Failure in Scope" on the monitor 4 as a notification.

When the JTAG chain is CLOSE (No), at step S19, a check is performed on the next part.
<Step S19>
The test pattern generating section 27 of the pre-processing circuit 20 outputs a test pattern signal.
<Step S20>
The output-detection circuit 31 detects the presence or absence of an output of the test pattern signal from the pre-processing circuit 20. That is, the step S20 is a digital image pickup signal detection step for detecting an image pickup signal from the endoscope 2, that is, the presence or absence of an output of the digital image pickup signal, and also is a test pattern signal detection step for detecting the presence or absence of a test pattern signal.

When the output-detection circuit 31 detects no outputted test pattern signal from the pre-processing circuit 20 (No), the process goes to step S21 because the problem is known to exist in pre-processing circuit 20 or a video processing circuit 36 of the post-processing circuit 30 after the connections in the post-processing circuit 30 and the endoscope 2 are already checked.

To the contrary, when the output-detection circuit 31 detects an outputted test pattern signal from the pre-processing circuit 20 (Yes), the process goes to step S25.
<Step S21>
The endoscope system 1 makes a switching to the capture circuit 37 between the post-processing circuit 30 and the capture circuit 37.
<Step S22>
When the output-detection circuit 31 cannot detect any outputted signal to the monitor 4 even through the capture circuit 37 (No), it is determined that the pre-processing circuit 20 has a failed part, and at step S23, the notifying circuit 38 displays "Failure in Pre-Processing Circuit" on the monitor 4 as a notification.

To the contrary, when the output-detection circuit 31 is able to detect an outputted signal to the monitor 4 through the capture circuit 37 (Yes), it is determined that the video processing circuit 36 has a failed part, and at step S24, the notifying circuit 38 displays "Failure in Video Processing" on the monitor 4 as a notification.
<Step S25>
At step S20, when the output-detection circuit 31 detects an outputted test pattern signal from the pre-processing circuit 20 (Yes), a check on the outputting system of the CCD 6 is performed. An analog image pickup signal from the CCD 6 is converted to a 12-bit digital image pickup signal by the AFE 25 that includes the CDS circuit 23 and the AD converter circuit 24, to be outputted to the FPGA 29.
<Step S26>
The FPGA 29 outputs the 12-bit digital image pickup signal from the AFE 25 to the post-processing circuit 30. Here, a switching is made to the post-processing circuit 30 between the post-processing circuit 30 and the capture circuit 37.
<Step S27>
When the output-detection circuit 31 is able to detect an outputted signal from the CCD 6 (Yes), it is determined that the CCD 6 does not have any failed part, and the process goes to step S32.

To the contrary, when the output-detection circuit 31 is not able to detect any outputted signal from the CCD 6 (No), the process goes to step S28.
<Step S28>
The endoscope system 1 makes a switching to the capture circuit 37 between the post-processing circuit 30 and the capture circuit 37.
<Step S29>
When the output-detection circuit 31 is not able to detect any outputted signal to the monitor 4 even through the capture circuit 37 (No), it is determined that the CCD 6 has a failed part, and at step S30, the notifying circuit 38 displays "Failure in CCD" on the monitor 4 as a notification.

To the contrary, when the output-detection circuit 31 is able to detect an outputted signal to the monitor 4 through the capture circuit 37 (Yes), it is determined that the video processing circuit 36 has a failed part, and at step S31, the notifying circuit 38 displays "Failure in Video Processing" on the monitor 4 as a notification.
<Step S32>
The endoscope system 1 finally checks the AFE 25 for failure when there is no problem in the CCD 6, the pre-processing circuit 20, and the post-processing circuit 30.

In the final check, the AFE-detection section 26 checks digital signal data for a so-called bit drop. For example, when a digital image pickup signal is supposed to have a predetermined number 12 of bits, the resulting data with a bit drop has 11 bits or less.
<Step S33>
When finding a bit drop (No), the AFE-detection section 26 determines that the AFE 25 is the failed part, and at step S31, the notifying circuit 38 displays "Failure in AFE" on the monitor 4 as a notification. That is, the step S33 is an AFE-detection step for detecting that the AFE 25 is normally operating when the number of bits of a digital image pickup signal is equal to a predetermined number of bits.
<Step S34>
Without any detection of failed part in the above described entire processings, the operation of the endoscope system 1 is determined to be normal, and the notifying circuit 38 displays "Normally Operating" on the monitor 4 as a notification.
<Step S35>

The endoscope system 1 ends the maintenance mode, and starts a normal operation. To the contrary, with any detection of a failed part in the maintenance mode, that is, in the case (I) of FIG. 4A or FIG. 4B, the endoscope system 1 does not start a normal operation and wait for a response from an operator.

In the above description, the endoscope system 1 automatically enters in a maintenance mode at the time of startup, but may go into a maintenance mode in response to an instruction from an operator after the endoscope system 1 starts a normal operation. Alternatively, the endoscope system 1 may be set not to automatically enter in a maintenance mode at the time of startup, but go into a maintenance mode in response to an instruction from an operator.

Also, in the above description, the maintenance mode is explained as being controlled by the endoscope system 1, but more specifically, the maintenance mode is controlled by a control section (not shown) that controls the endoscope system 1 as a whole. The circuits such as the output-detection circuit 31 and the notifying circuit 38 may be included in the control section.

As described above, in the endoscope system 1 which is an image pickup system of the present embodiment, a failed part is easily determined, and the determination of a failed part is facilitated using the method for maintaining the endoscope system 1 which is a method for maintaining an image pickup system of the present embodiment.

In addition, in the above description, the endoscope system 1 detects six failed parts therein, including: a failure in post-processing circuit, a connection failure in scope, a failure in pre-processing circuit, a failure in video processing, a failure in CCD, and a failure in AFE, but even in an endoscope system that detects one or more failed parts selected from the six parts, the failed part(s) can be easily determined.

As described above, a method for maintaining an image pickup system of the present embodiment is a method for maintaining the endoscope system 1 which is an image pickup system having the endoscope 2 as an image pickup apparatus for picking up an image of the subject 10 and outputting an image pickup signal of the image, and the external processor 3 which is a signal processing apparatus having the post-processing circuit 30 as a signal processing circuit for processing the image pickup signal inputted from the endoscope 2 via an electrically connectable connector section 8 and outputting a video signal that can be outputted to the monitor 4 as a signal processing circuit, and the method includes: a video signal detection step for detecting the presence or absence of an output of the video signal; a connection-detection step for detecting the presence or absence of an electrical connection at the connector section 8; and an image pickup signal detection step for detecting the presence or absence of an output of the image pickup signal.

Second Embodiment

Now, with reference to FIG. 5 and FIG. 6, an endoscope system 1B which is an image pickup system of a second embodiment according to the present invention will be explained below. The endoscope system 1B of the present embodiment B is similar to the endoscope system 1 of the first embodiment, and the same elements are denoted by the same reference numerals, which will not be explained below.

Figure 5:
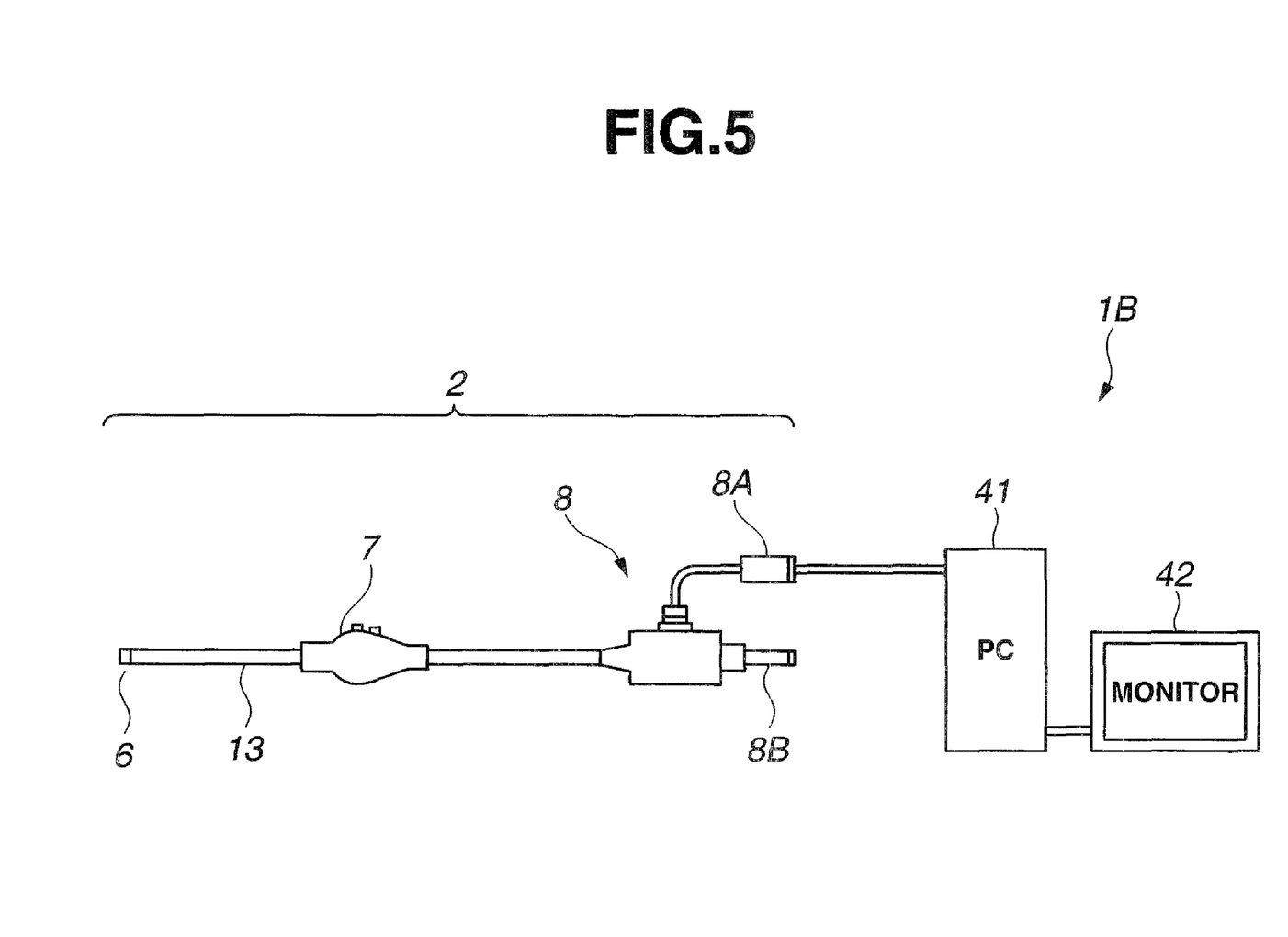
FIG. 5 is an illustrative diagram illustrating a configuration of an endoscope system of a second embodiment.
Figure 6:
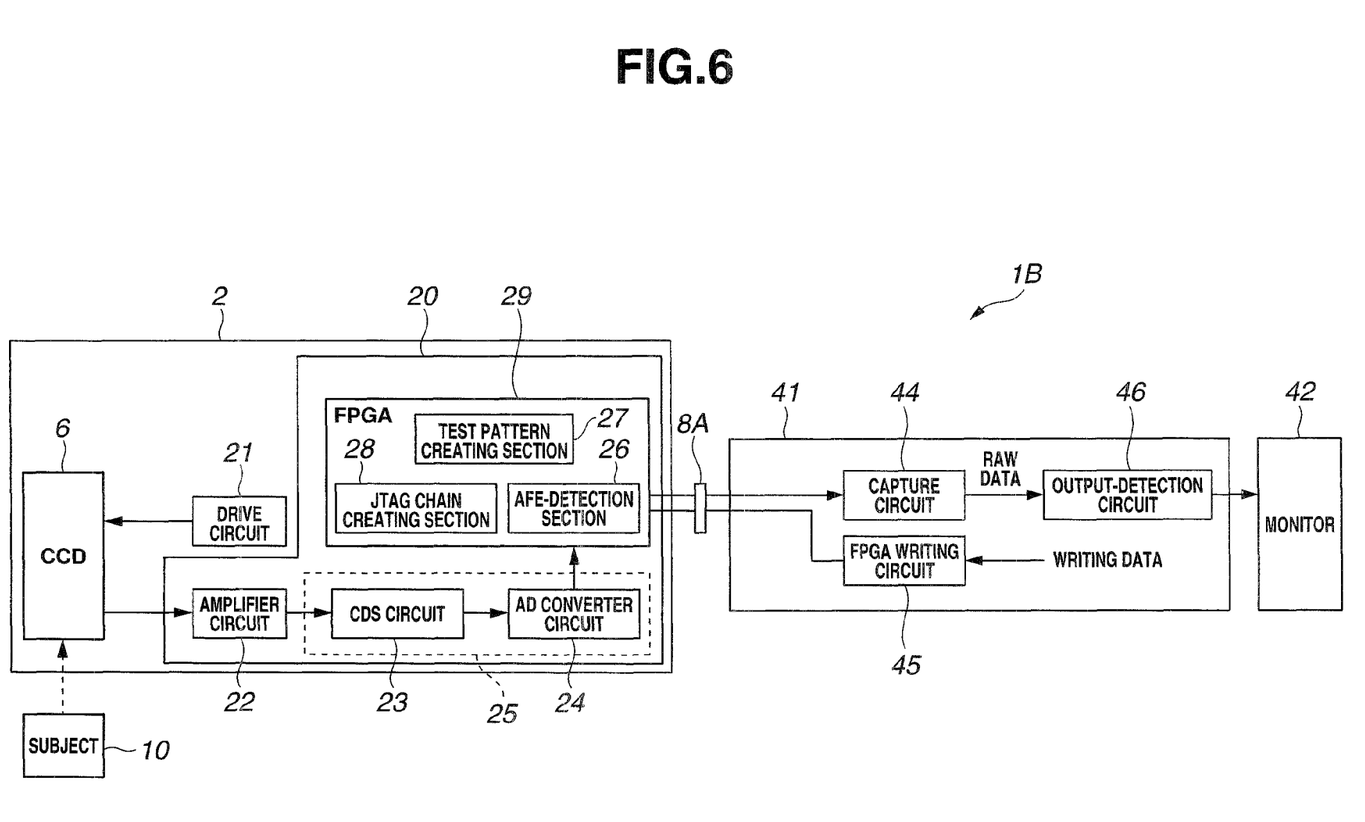
FIG. 6 is a block diagram illustrating a configuration of the endoscope system of the second embodiment.

FIG. 5 is an external view illustrating the endoscope system 1B of the present embodiment, and FIG. 6 is a block diagram illustrating a configuration of the endoscope system 1B of the present embodiment.

The endoscope 2 shown in FIG. 5 is similar to the endoscope 2 of the first embodiment, except that the endoscope 2 is not connected to the external processor 3 and the light source apparatus 5 that are designed for exclusive use with the endoscope 2, but is connected to a PC 41. The PC 41 may be a general-purpose personal computer (PC) for example, and includes a CPU (Central Processing Unit) to provide functions such as ones for processing desired data in accordance with software installed therein.

The endoscope 2 is able to output digital image pickup signals by itself. So, the endoscope 2 can be connected to a digital equipment such as a PC, other than the external processor 3 designed for exclusive use with endoscope apparatuses, to be used. In such a use form also, in the endoscope system 1B of the present embodiment, any failed part in the endoscope 2 can be easily determined.

That is, during a treatment using an endoscope, even if an abnormal vision is observed in an image picked up by the endoscope, sometimes the treatment should be continued using the endoscope. In the case, an operator uses a spare endoscope, that is, the failed endoscope is removed from the external processor 3, and the spare endoscope is connected to the external processor 3, which makes it impossible to determine a failed part of the failed endoscope using the external processor 3.

However, in the case of the endoscope system 1B of the second embodiment of the present invention, as shown in FIG. 5, an operator can connect the endoscope 2 to the PC 41 via the connector section 8A, which makes the determination of a failed part possible. When the PC 41 cannot be directly connected to the connector section 8A, a converter may be interposed between the PC 41 and the connector section 8A for connection.

In addition, when the software for internal processing circuits of the endoscope 2 such as the FPGA 29 is updated, or when the transmission cable has a shorter length due to repairing of a breakage of the cable, the connection of the PC 41 to the endoscope 2 enables an appropriate update of the setting installed in the endoscope to response to the cable length.

That is, in the endoscope system 1B of the present embodiment, a determination of a failed part in the endoscope 2 is easily achieved without using the external processor 3 which is designed for exclusive use with the external processor 3, and also even if the endoscope 2 is not failed, a maintenance of the endoscope 2 such as updating of software therein can be implemented.

Furthermore, as shown in FIG. 6, the endoscope system 1B of the present embodiment has the PC 41 and a monitor 42. The PC 41 includes: a capture circuit 44 for processing digital image pickup signals; an FPGA writing circuit 45 for writing data into the FPGA of the endoscope 2; and an output-detection circuit 46 which is an output-detection section for detecting a failed part in the endoscope 2.

In the endoscope system 1B, when the endoscope 2 is connected to the PC 41, a normal display of an image picked up by the endoscope on the monitor 42 indicates that a failed part is included in the external processor, and not included in the endoscope 2. Also, in the endoscope system 1B, a failed part in the endoscope 2 can be determined. That is, the output-detection circuit 46 of the PC 41 is able to detect three failed parts, including: a failure in pre-processing circuit, a failure in CCD, and a failure in AFE. Needless to say, even if the endoscope system 1B is configured to detect one or more failed parts selected from the three parts, the failed part(s) can be easily determined.

In the endoscope system 1B also, a connection failure in scope can be detected using the JTAG chain creating section 28 of the FPGA 28.

The endoscope 2 of the present embodiment is able to easily output RAW data of sequential still images to the monitor 4 via the capture circuit 44.

Furthermore, in the endoscope 2 of the present embodiment, maintenance operations such as updating of software therein can be implemented via the FPGA writing circuit 45 in the PC 41.

That is, the PC 41 is provided with a function to switch between a mode for determining a failed part in the endoscope 2 and a normal mode, and the switching operation is performed using a user interface such as a keyboard (not shown) connected to the PC 41.

When the PC 41 has a communication section therein, the PC 41 is able to obtain data such as software contents of the endoscope 2 and software for maintenance through the Internet. Also, the PC 41 enables any updating of the software for the endoscope 2 from a remote service center through the Internet.

Modified Example of Second Embodiment

Figure 7:
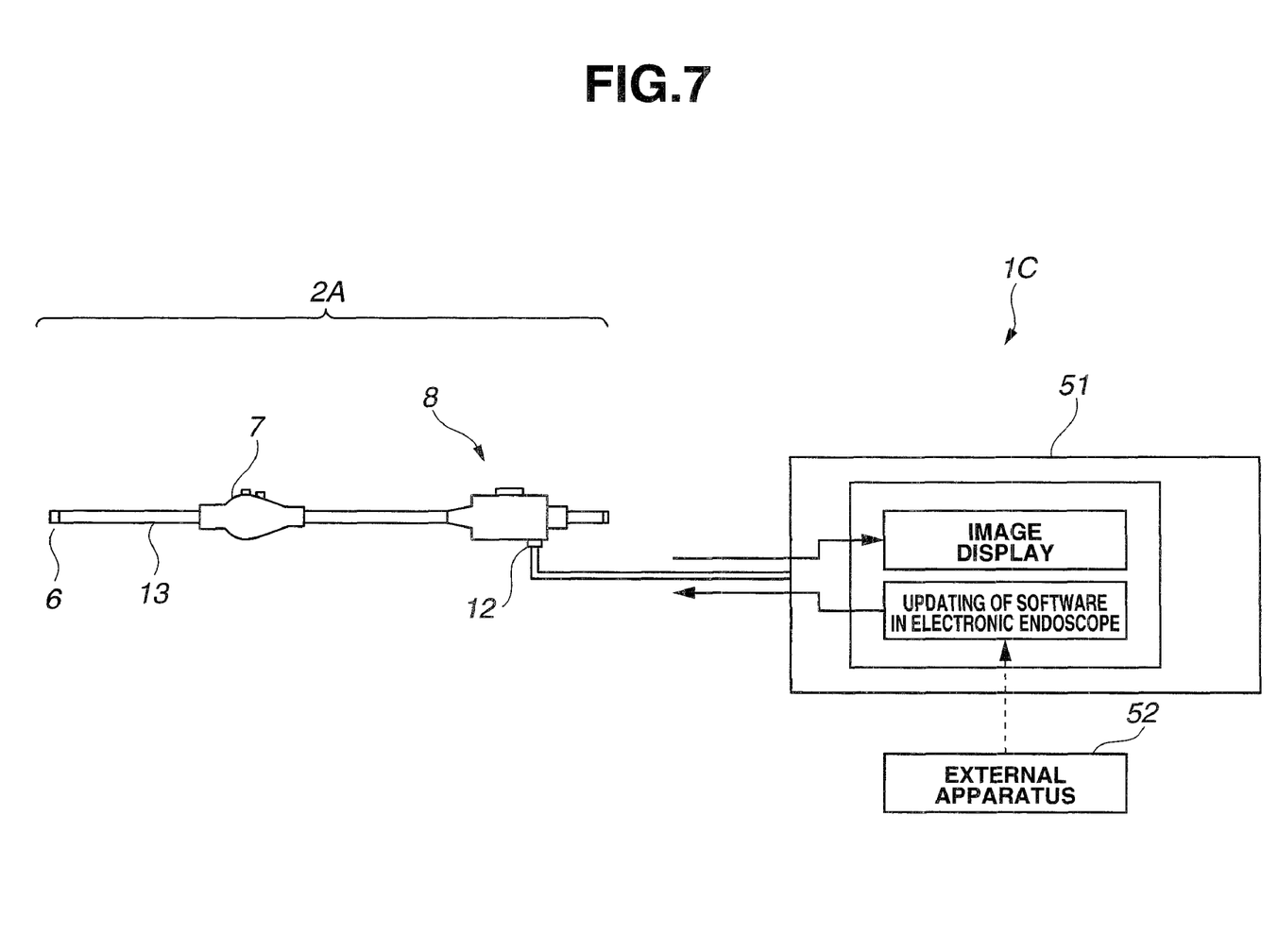
FIG. 7 is an illustrative diagram illustrating a configuration of an endoscope system of a modified example of the second embodiment.

Now, with reference to FIG. 7, an endoscope system 1C which is an image pickup system of a modified example of the second embodiment according to the present invention will be explained below. The endoscope system 1C of the present modified example is similar to the endoscope system 1 of the first embodiment, and the same elements are denoted by the same reference numerals, which will not be explained below. FIG. 7 is an illustrative diagram for illustrating the endoscope system 1C of the present modified example.

In the endoscope system 1C shown in FIG. 7, an endoscope 2A has a parallel port terminal 12 at the connector section 8 thereof for a connection with a PC 5. Thus, the endoscope 2A can be easily connected to a parallel port terminal of the PC 51 such as a printer board. The PC 51 is able to obtain data that is necessary for detecting a failed part in the endoscope 2A or updating of software for the endoscope 2A from an external apparatus 52. The external apparatus 52 may be a playback apparatus for storage media, or an apparatus that can be connected to a network and obtains necessary data from the network.

Because the endoscope 2A is provided with the general-purpose parallel port terminal 12 in addition to the advantages of the endoscope 2, the endoscope 2A can be easily connected to various pieces of general-purpose digital equipment, which facilitates the determining of a part to repair, and also the output of RAW data of sequential still images to the monitor 42.

Third Embodiment

Figure 8:
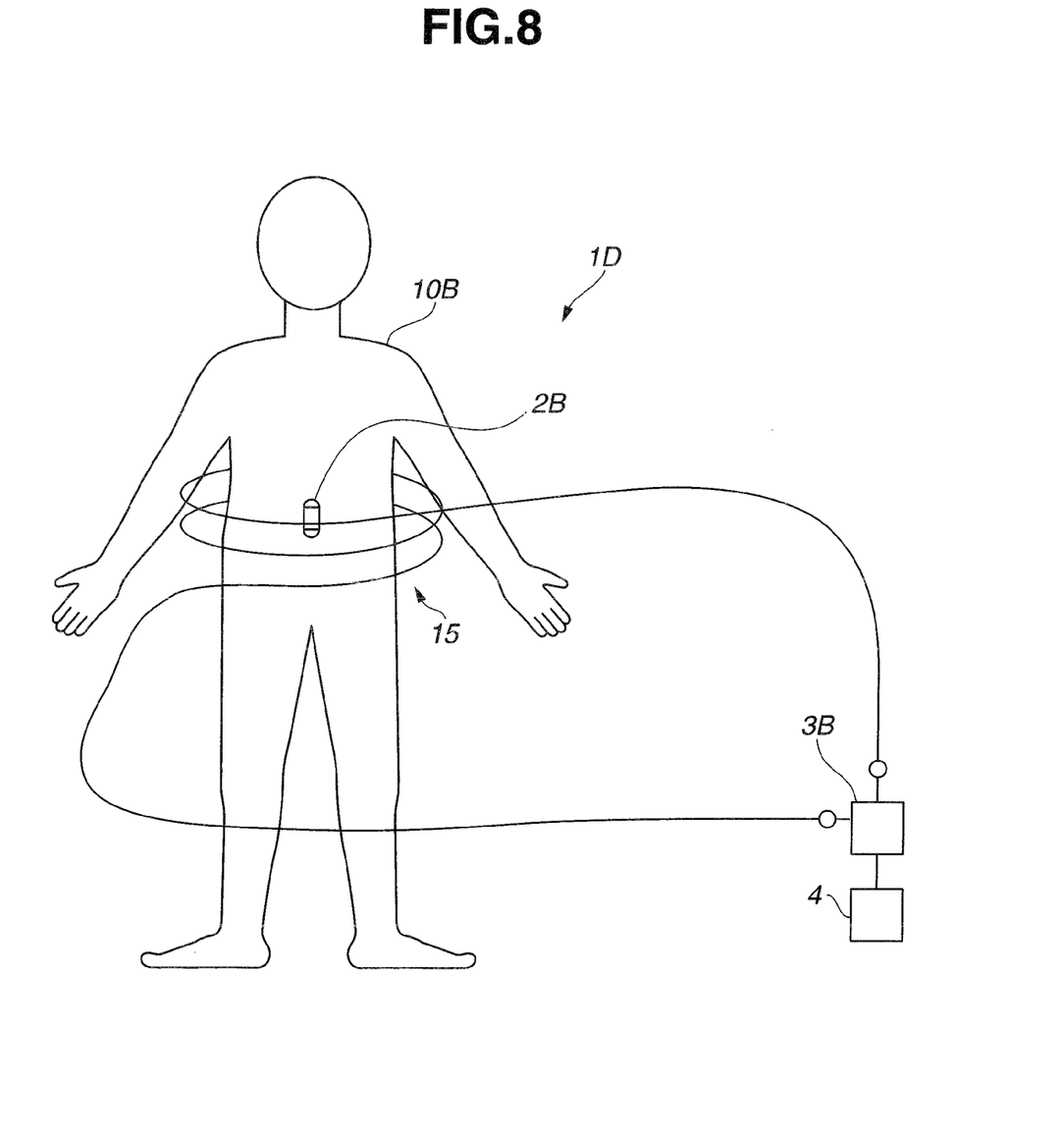
FIG. 8 is a conceptual diagram illustrating a use form of an endoscope system of a third embodiment.

Now, with reference to FIG. 8 and FIG. 9, an endoscope system 1D of a third embodiment according to the present invention will be explained below. The endoscope system 1D of the present embodiment is similar to the endoscope system 1 of the first embodiment, and the same elements are denoted by the same reference numerals, which will not be explained below. FIG. 8 is a conceptual diagram illustrating a use form of the endoscope system 1D of the present embodiment, and FIG. 9 is a block diagram illustrating a configuration of the endoscope system 1D of the present embodiment.

As shown in FIG. 8, the endoscope 2B of the present embodiment is a so-called capsule endoscope. The capsule endoscope 2B is configured so that, after swallowed by a subject 10B who is an object of observation or examination, the capsule endoscope 2B moves through the organs such as stomach and small intestine by peristaltic movement until the spontaneous elimination so that the capsule endoscope 2B picks up images of the inside of the organs in series with the function for image pickup.

The images picked up by the capsule endoscope 2B are transmitted to an external processor 3B via radio communication and through a receiving coil 15 that is disposed outside of the body of the subject 10B, to be displayed on the monitor 4.

Figure 9:
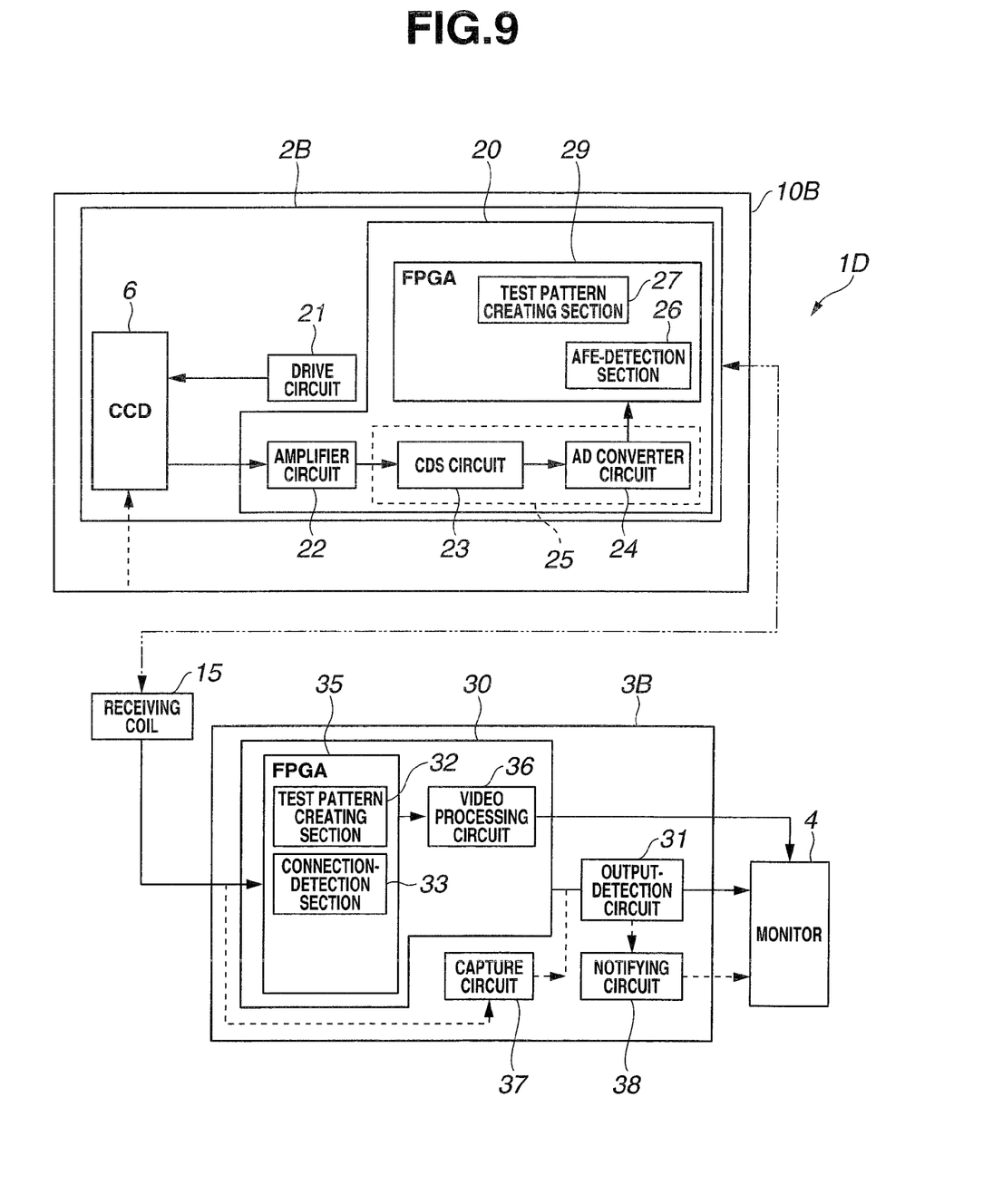
FIG. 9 is a block diagram illustrating a configuration of the endoscope system of the third embodiment.

That is, as shown in FIG. 9, the CCD 6 of the endoscope 2B picks up images in the subject 10B while moving through the organs, and the analog image pickup signals of the images are converted to digital image pickup signals by the pre-processing circuit 20 of the endoscope 2B, and transmitted to the outside of the body through a radio transmitting section. The digital image pickup signals transmitted to the outside of the body are inputted to the external processor 3B through a radio receiving section, and processed by the post-processing circuit 30 to be displayed on the monitor 4.

As compared to the endoscope system 1 of the first embodiment, the endoscope system 1D has configurations, operations, and effects similar to those of the endoscope system 1 of the first embodiment, except the difference in the means for transmitting image pickup signals from the endoscope 2B to the external processor 3 between wire and wireless.

That is, the endoscope system 1D is able to detect five failed parts, including: a failure in post-processing circuit, pre-processing circuit, a failure in video processing, a failure in CCD, and a failure in AFE. In the endoscope system 1D, the connection-detection section 33 detects a failure of the receiving coil 15 such as disconnection, which results in a detection of a connection failure.

As described above, the endoscope system 1D is an image pickup system in which a failed part can be easily determined.

Fourth Embodiment

Figure 10:
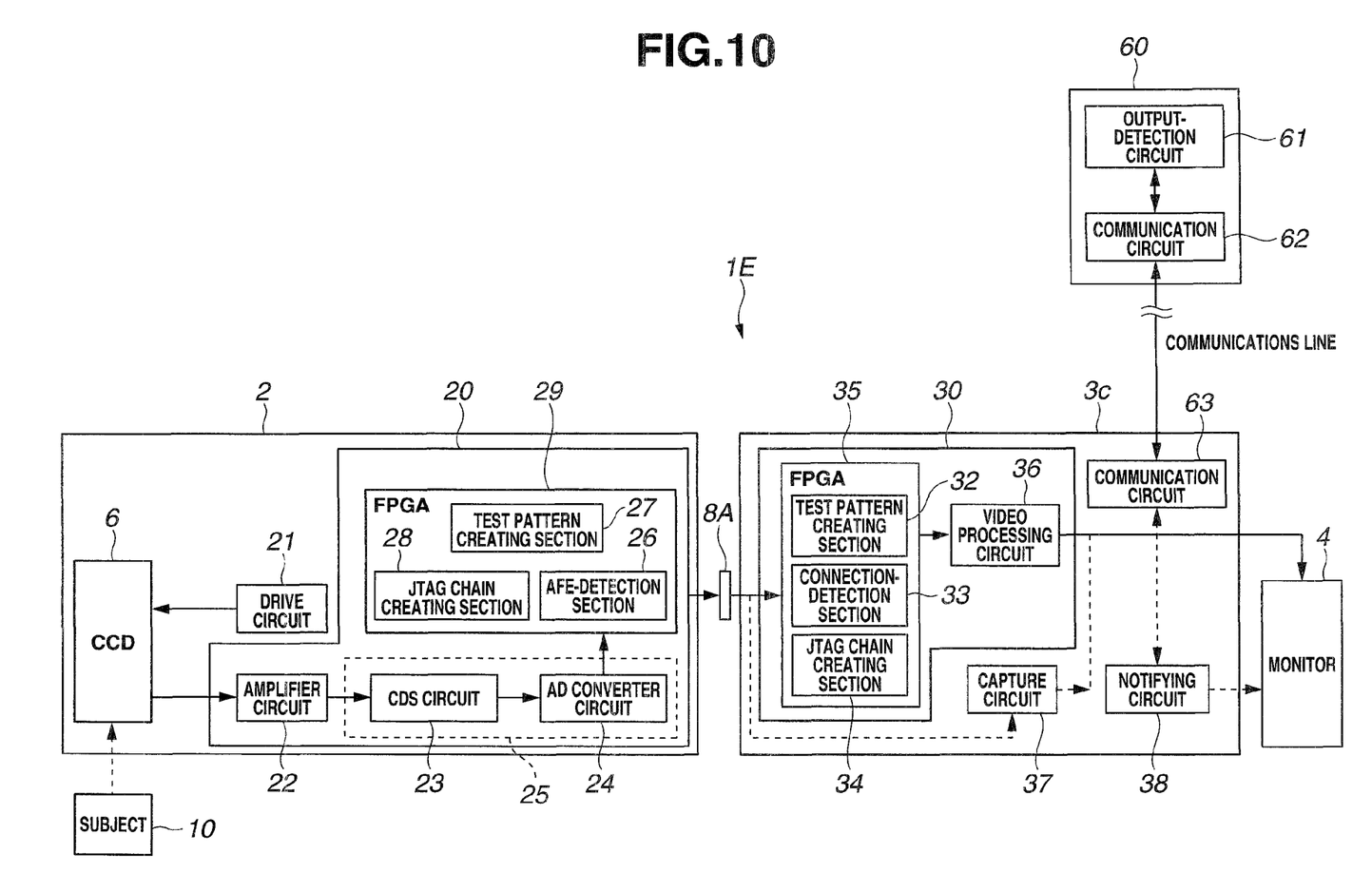
FIG. 10 is a block diagram illustrating a configuration of an endoscope system of a fourth embodiment.

Now, with reference to FIG. 10, an endoscope system 1E of a fourth embodiment according to the present invention will be explained below. The endoscope system 1E of the present embodiment is similar to the endoscope system 1 of the first embodiment, and the same elements are denoted by the same reference numerals, which will not be explained below. FIG. 10 is a block diagram illustrating a configuration of the endoscope system 1E of the present embodiment.

The endoscope 2 of the endoscope system 1E is similar to the endoscope 2 of the first embodiment. However, the external processor 3C is different from the external processor 3 of the first embodiment in that external processor 3C does not include any output-detection circuit. Instead, the external processor 3C of the endoscope system 1E has a communication circuit 63 as a communication section, so as to be connectable through a communications line to a communication circuit 62 of a detection apparatus 60 which is installed at another place. The detection apparatus 60 includes an output-detection circuit 61 and the like which are used to determine a failed part in the endoscope system 1E and perform maintenances such as updating of software. The detection apparatus 60 may be a PC.

That is, when the endoscope system 1E is connected to a communications line, a determination of a failed part in the endoscope system 1E or maintenance for every updating of software in the endoscope system 1E can be implemented from a remote place.

The communications line may be a known communications line such as the Internet connection and cell phone connection.

The endoscope system 1E provides the same advantages as those of the endoscope system 1 of the first embodiment, and also enables an easy determination of a failed part therein from a remote place.

In the above description, an endoscope was used as an image pickup apparatus, and an external processor or a PC were used as a signal processing apparatus, the present invention is not limited to an endoscope as long as the image pickup apparatus picks up an image of a subject and outputs an image pickup signal of the image, and is not limited to an endoscope external processor or a PC as long as the signal processing apparatus has a signal processing circuit that processes an image pickup signal inputted from an image pickup apparatus and is able to output a video signal to a monitor or the like. Similarly, an image pickup system and a method for maintaining the image pickup system of the present invention are not limited to an endoscope system and a method for maintaining the endoscope system.

Having described the preferred embodiments of the invention referring to the accompanying drawings, it should be understood that the present invention is not limited to those precise embodiments and that various changes and modifications thereof could be made by one skilled in the art without departing from the spirit or scope of the invention as defined in the appended claims.

What is claimed is:

1. An image pickup system, comprising:
   an image pickup apparatus for picking up an image of a subject and outputting an image pickup signal of the image;
   a signal processing apparatus having a signal processing circuit which processes the image pickup signal inputted from the image pickup apparatus and generates a video signal that can be outputted to a display section;
   an output-detection section for detecting the presence or absence of an output of the image pickup signal and the presence or absence of an output of the video signal;
   a connector section which is able to electrically connect the image pickup apparatus and the signal processing apparatus to each other; and
   a connection-detection section for detecting the presence or absence of an electrical connection at the connector section
   wherein the image pickup apparatus and the signal processing apparatus include first and second Field Programmable Gate Arrays (FPGAs) that are able to generate a Joint Test Action Group (JTAG) chain, respectively, and the connection-detection section detects the presence or absence of an electrical connection at the connector section using the JTAG chains created by the first and second FPGAs.

2. The image pickup system according to claim 1, wherein the image pickup apparatus comprises:
   an image pickup device for picking up an image of the subject and outputting an analog image pickup signal of the image;
   an analog front end that processes the analog image pickup signal and outputs a number of bits of a digital image pickup signal; and
   an Analog Front End (AFE)-detection section for detecting if the analog front end is normally operating or not.

3. The image pickup system according to claim 2, wherein the AFE-detection section detects a normal operation of the analog front end when the number of bits of the digital image pickup signal is equal to the predetermined number of bits.

4. The image pickup system according to claim 1, wherein the image pickup apparatus and the signal processing apparatus include first and second FPGAs that have a function to output a test pattern signal, respectively, and the output-detection section detects the presence or absence of at least one of the test pattern signals.

5. The image pickup system according to claim 2, further comprising:
   a notifying section for notifying at least one of the detection results from the output-detection section, the connection-detection section, and the AFE-detection section.

6. The image pickup system according to claim 1, wherein the image pickup apparatus is an endoscope, and the signal processing apparatus is an endoscope signal processing apparatus.

7. The image pickup system according to claim 6, wherein the endoscope is a capsule endoscope.

8. The image pickup system according to claim 2, wherein the signal processing apparatus includes a communication section, and at least one of the output-detection section, the connection-detection section, and AFE-detection section is able to be controlled via the communication section.

9. The image pickup system according to claim 1, wherein the image pickup apparatus is an endoscope, and the signal processing apparatus is a PC.

10. An image pickup system, comprising:
    an endoscope apparatus, having an endoscope for picking up an image of a subject and outputting an analog image pickup signal of the image, an analog front end for processing the analog image pickup signal and outputting a number of bits of a digital image pickup signal, an Ananlog Front End (AFE)-detection section for detecting if the analog front end is normally operating or not, and a first Field Programmable Gate Array (FPGA) that is able to generate a Joint Test Action Group (JTAG) chain;
    an endoscope signal processing apparatus, having a signal processing circuit for processing the image pickup signal inputted from the endoscope apparatus and generating a video signal that can be outputted to a display section, and a second FPGA that is able to generate a JTAG chain;
    an output-detection section for detecting the presence or absence of an output of the image pickup signal, and the presence or absence of an output of the video signal;
    a connector section that is able to electrically connect the endoscope apparatus and the endoscope signal processing apparatus to each other;
    a connection-detection section for detecting the presence or absence of an electrical connection at the connector section using the JTAG chains by the first and second FPGAs; and
    a notifying section for notifying at least one of the detection results of the output-detection section, the connection-detection section, and the AFE-detection section.

11. The image pickup system according to claim 10, wherein the AFE-detection section detects a normal operation of the analog front end when the number of bits of the digital image pickup signal is equal to the predetermined number of bits.

12. The image pickup system according to claim 10, wherein the image pickup apparatus and the signal processing apparatus include first and second FPGAs that have a function to output a test pattern signal, respectively, and the output-detection section detects the presence or absence of at least one of the test pattern signals.

13. The image pickup system according to claim 10, wherein the signal processing apparatus includes a communication section, and at least one of the output-detection section, the connection-detection section, and AFE-detection section is able to be controlled via the communication section.

14. A method for maintaining an image pickup system that includes an image pickup apparatus and a signal processing apparatus, comprising:
 a video signal detection step for detecting the presence or absence of an output of a video signal from a signal processing apparatus having a signal processing circuit that processes the video signal inputted from the image pickup apparatus for picking up an image of a subject and outputting an image pickup signal of the image via an electrically connectable connector section and outputs the video signal that can be outputted to a display section;
 a connection-detection step for detecting the presence or absence of an electrical connection at the connector section; and
 an image pickup signal detection step for detecting the presence or absence of an output of the image pickup signal
 wherein the image pickup apparatus and the signal processing apparatus include first and second Field Programmable Gate Arrays (FPGAs) that have a function to output a test pattern signal, respectively, and the method further comprising:
 a test pattern signal detection step for detecting the presence or absence of each of the test pattern signals;
 wherein the first and second Field Programmable Gate Arrays (FPGAs) are able to generate a Joint Test Action Group (JTAG) chain, respectively, and the connection-detection section detects the presence or absence of an electrical connection at the connector section using the JTAG chains created by the first and second FPGAs.

15. The method for maintaining an image pickup system according to claim 14, wherein the image pickup apparatus comprises:
 an image pickup device for picking up an image of a subject and outputting an analog image pickup signal of the image; and
 an analog front end for processing the analog image pickup signal and outputting a number of bits of a digital image pickup signal, and the method further comprising:
 an Analog Front End (AFE)-detection step for detecting a normal operation of the analog front end when the number of bits of the digital image pickup signal is equal to the predetermined number of bits.

16. The method for maintaining an image pickup system according to claim 15, further comprising:
 a notifying step for notifying at least one of the detection results in the video signal detection step, the connection-detection step, the image pickup signal detection step, the AFE-detection step, and the test pattern signal detection step.

17. The method for maintaining an image pickup system according to claim 14, wherein the image pickup apparatus is an endoscope, and the signal processing apparatus is an endoscope signal processing apparatus.

* * * * *